(12) United States Patent
Rankin

(10) Patent No.: US 8,163,011 B2
(45) Date of Patent: Apr. 24, 2012

(54) INTRA-ANNULAR MOUNTING FRAME FOR AORTIC VALVE REPAIR

(75) Inventor: J. Scott Rankin, Nashville, TN (US)

(73) Assignee: Biostable Science & Engineering, Inc., Austin, TX (US)

( * ) Notice: Subject to any disclaimer, the term of this patent is extended or adjusted under 35 U.S.C. 154(b) by 179 days.

(21) Appl. No.: 11/799,942

(22) Filed: May 3, 2007

(65) Prior Publication Data

US 2008/0086204 A1     Apr. 10, 2008

Related U.S. Application Data

(60) Provisional application No. 60/849,919, filed on Oct. 6, 2006.

(51) Int. Cl.
*A61F 2/24* (2006.01)
(52) U.S. Cl. ........................................ 623/2.36; 623/2.1
(58) Field of Classification Search ................ 623/2.11, 623/2.14, 2.16, 2.17, 2.18, 2.13, 900, 2.1, 623/1.26, 1.24, 2.36–2.39
See application file for complete search history.

(56) References Cited

U.S. PATENT DOCUMENTS

| | | | |
|---|---|---|---|
| 3,548,418 A | 12/1970 | Angell et al. | |
| 3,714,671 A | 2/1973 | Edwards et al. | |
| 4,451,936 A | 6/1984 | Carpentier et al. | 3/1.5 |
| 4,501,030 A | 2/1985 | Lane | |
| 5,258,021 A | 11/1993 | Duran | 623/2 |
| 5,607,471 A | 3/1997 | Seguin et al. | |
| 5,910,170 A | 6/1999 | Reimink et al. | |
| 6,231,602 B1 | 5/2001 | Carpentier et al. | 623/2.4 |
| 6,258,122 B1 | 7/2001 | Tweden et al. | 623/2.4 |
| 6,610,088 B1 | 8/2003 | Gabbay | 623/2.4 |
| 6,767,362 B2 | 7/2004 | Schreck | 623/2.11 |
| 2002/0138138 A1* | 9/2002 | Yang | 623/2.18 |
| 2003/0093147 A1 | 5/2003 | Ogle et al. | |
| 2005/0149181 A1* | 7/2005 | Eberhardt | 623/2.14 |
| 2005/0228494 A1 | 10/2005 | Marquez | |
| 2005/0246014 A1 | 11/2005 | McCarthy | |
| 2006/0015179 A1 | 1/2006 | Bulman-Fleming et al. | |
| 2006/0020332 A1 | 1/2006 | Lashinski et al. | |
| 2009/0054973 A1 | 2/2009 | Johnson | |
| 2009/0177271 A1 | 7/2009 | Fabiani | |

FOREIGN PATENT DOCUMENTS

| | | |
|---|---|---|
| GB | 1264472 | 2/1972 |
| WO | 9716135 | 5/1997 |
| WO | 0062715 A1 | 10/2000 |
| WO | 03041617 A1 | 5/2003 |
| WO | 2008133852 A1 | 11/2008 |

OTHER PUBLICATIONS

U.S. Appl. No. 60/849,919, filed Oct. 6, 2006, by Scott Rankin, M.D.

* cited by examiner

*Primary Examiner* — Thomas J Sweet
*Assistant Examiner* — Matthew Schall
(74) *Attorney, Agent, or Firm* — Waddey & Patterson, P.C.; Ryan D. Levy

(57) ABSTRACT

An intra-annular mounting frame for an aortic valve having native aortic cusps is provided which includes a frame body with native leaflet reorienting curvatures and interconnecting points; the curvatures shaped to be received inside the valve below the native aortic cusps and to reorient the native aortic cusps within the aortic valve, where each of the curvatures extends concavely upward from a reference latitudinal plane tangential to each curvature's base.

24 Claims, 7 Drawing Sheets

INTRA-ANNULAR MOUNTING FRAME FOR AORTIC VALVE REPAIR

The present application is a continuation of and claims benefit of our U.S. provisional patent application Ser. No. 60/849,919, entitled "Intra-Annular Ring For Aortic Valve Repair" filed Oct. 6, 2006 and is hereby incorporated by reference. Additionally all patents and publications described or discussed herein are hereby incorporated by reference in their entireties.

BACKGROUND OF THE INVENTION

1. Technical Field

The present invention relates to a mounting frame useful for applications including aortic valve repair. More particularly, the present invention relates to an intra-annular mounting frame which is inserted directly into the aortic valve annulus. The invention also includes methods for the insertion and implantation of the intra-annular mounting frame, as well as complementary devices, such as ascending aortic Dacron® grafts and pericardial single cusp prostheses.

2. Background of the Art

The mammalian heart is essentially a pump that functions as a chemo-mechanical energy transducer. The chemical energy of metabolic substrates and oxygen is converted into the mechanical energy of blood pressure and flow by myocardial sarcomeres during cardiac contraction. The pump is periodic at a frequency of 1-2 Hz, with the contraction/ejection phase called systole and the relaxation/filling phase termed diastole.

The human heart is the center of the cardiovascular system, the system having two parallel circulations consisting of the pulmonary circulation and the systemic circulation. The pulmonary circulation receives blood from the venae cavae into the right atrium and right ventricle, and then pumps the cardiac output into the pulmonary arteries and through the lungs. The systemic circulation receives blood from the pulmonary veins, pumps the cardiac output through the left atrium and left ventricle to the aorta, systemic arteries, capillaries, and veins, and finally transmits blood back to the venae cavae. The mitral valve is positioned between the upper chamber, the left atrium, and the pumping chamber, the left ventricle. The left atrium acts in a capacitor function receiving blood from the lungs via the pulmonary veins throughout the cardiac cycle. The left ventricle fills during diastole by receiving blood from the left atrium as the mitral valve opens, and then during systole, the mitral valve closes and permits forward ejection of the blood from the left ventricle into the ascending aorta. The aortic valve is located between the left ventricle and aorta, and functions under normal conditions to allow unimpeded blood flow out of the ventricle and into the aorta during systole. During diastole, the aortic valve closes and prevents regurgitation backward into the left ventricle.

Surgical reconstruction of a patient's native valve is becoming standard for mitral valve disease. Whether considering mitral valve prolapse, pure annular dilatation, ischemic mitral regurgitation, or mitral endocarditis, repair is now routine, highly successful, and associated with low late failure rates. Even in rheumatic mitral disease, many surgeons are embarking on programs of aggressive repair, adding to ring annuloplasty the techniques of posterior leaflet augmentation with gluteraldehyde-fixed autologous pericardium, resection of the stenotic submitral apparatus with insertion of artificial Gortex® chords, leaflet decalcification, etc. The current goal is to achieve close to a 100% repair rate of mitral valve disorders and to markedly diminish prosthetic valve replacement. The advantages of repair versus replacement in this setting are well documented. The operative mortality rate (normalized for other factors) is lower, anticoagulation is not required in sinus rhythm, valve-related complications are less than with prosthetic valves, durability is excellent because the patient's own tissues do not degenerate, and late endocarditis is reduced because less foreign material is present. As such, these concepts for mitral valve disease are rapidly becoming standard-of-care in the field of cardiac surgery.

The aortic valve of a human heart can also become diseased, with aortic valve insufficiency occurring from a number of causes. A common cause is annular dilatation, with the sinuses of the Valsalva migrating outward and the inter-commissural distances expanding. Geometrically, this derangement not only increases the annular circumference, but also reduces the surface area of cusp coaptation. The coaptation angle of the cusps is changed essentially from being parallel and meeting at an acute angle to pointing at each other, wherein the cusps comprise a more obtuse arrangement. Eventually, a central gap of coaptation occurs and increasing aortic insufficiency begets more annular dilatation which begets more aortic insufficiency and the leak progressively increases.

Repair of a diseased aortic valve has not been met with the same success as experienced in reconstructing a diseased mitral valve. For about 10 to 15 years, the "commissural annuloplasty" technique has been used, but it can only be applied to mild-to-moderate secondary aortic insufficiency, usually in patients undergoing primary coronary bypass or mitral valve procedures. Commissural annuloplasty not only decreases annular circumference, but also tends to move the sinuses centrally, thus normalizing geometry and coaptation angles of the cusps. There is a limit, however, to the geometric abnormality that commissural annuloplasty can normalize, and because the entire annulus is not fixed by this procedure, the potential for further dilatation and recurrent aortic insufficiency exists. As such, other devices and methods have been proposed including, for example, Carpentier et al. (U.S. Pat. No. 4,451,936) which teaches a supra-annular aortic valve. According to Carpentier et al., the invention is applicable to mechanical heart valves and leaflet-type heart valves, and does not project into the aortic valve.

In Duran et al., U.S. Pat. No. 5,258,021, an annuloplasty ring is described for insertion inside the aorta in the supra-annular region above the aortic valve annulus. The disclosed device appears circular from above and has three substantially sinusoidal shaped struts.

U.S. Pat. No. 6,231,602, Carpentier et al. describes an annuloplasty ring sutured to the tissue above the aortic valve annulus and also an infra-annular ring which can be sutured to the dense tissue immediately below the commissural-arterial wall intersection. Moreover, the infra-annular ring does not alter or even influence leaflet geometry in an organized manner, but instead constricts the infra-annular aorta to move the inferior aspects of the leaflets centrally rather than restore proper leaflet coaptation. Furthermore, as the ring of the '602 patent is apparently based on previous studies of the mitral valve, the '602 neglects the complexities of the 3-dimensional geometry of the aortic valve and ineffectively constricts either the supra-valvular or infra-valvular area. Also, the '602 patent describes the ring as only following the rough shape of the aortic tissue either above or below the valve annulus and neither provides an explanation of the proper sizing of the ring nor describes how the ring will be implanted within the patient.

In Marquez, U.S. Published Patent Application No. 2005/0228494, a heart valve frame is described which can separate into a plurality of individual cusps after implantation. Additionally, the invention of the '494 patent application is preferably used with synthetic leaflets.

Unfortunately, supra- or infra-annular rings and artificial valves of the prior art processes are generally not effective for the long term improvement of the aortic valve, and additionally, may require quite complicated surgical procedures. The rings currently described for insertion into the aorta are designed to be inserted above or below the valve. Suturing a ring below the aortic valve (infra-annular) to simply downsize or constrict the circumference will negatively distort the valve cusps and can lead to worsening valve leak. Furthermore, the constriction concept ignores the fact that the three semi-lunar aortic valve cusps are three-dimensional structures that are required to meet in space in a specific orientation to provide valve competence. Similarly, the supra-annular rings of the prior art are laden with the same problems, and have even less geometric basis, since the supra-annular rings only quite roughly follow the shape of the aortic tissue above the annulus and are based on no tangible geometric model.

What is desired, therefore, is a mounting frame which is inserted directly into the aortic valve annulus to repair the aortic valve. Indeed, a combination of characteristics, including a scientifically generated model incorporating the three-dimensional aspects of the aortic valve, has been found to be necessary for returning aortic valvular geometry to normal. Also desired is a process for inserting and mounting such frames.

SUMMARY OF THE INVENTION

The present invention provides an intra-annular hemispherical mounting frame which is uniquely adapted to the three-dimensional characteristics of the aortic valve. The intra-annular hemispherical mounting frame exhibits a design with careful consideration toward the anatomical features of the aortic valve anatomy so that valve competence is restored.

In developing the intra-annular hemispherical mounting frame, multiple human cadaver hearts were dissected and subsequently opened longitudinally through the commissure between the left and right coronary cusps. The specimens were pinned flat and measured with the annular circumference being the linear distance from one aortic margin to the other at the base of the cusps. With the annular circumference known, both the annular diameter and the radius of the valve were determined through standard circle mathematics including the equation $C=\pi D=2\pi r$.

Generally the intercommissural linear distance of each cusp (C/3) was found to roughly approximate the annular diameter of the aortic valve (C/3.14), and the height of each cusp consistently was within about 1 millimeter of the radius of the valve. Additionally, each cusp maintained a more "shield-like" shape at the free edge with the upper aspect being slightly thicker than the rest of the leaflet. Also, the upper aspects of the leaflets at the lateral surface were flattened in a crescent shape, tapering toward the center of the leaflet and also at the commissural insertion, creating areas of coaptation, referred to herein as "coaptation crescents."

With the above observations, the aortic valve was circularly modeled as illustrated in FIG. 1. More specifically, the aortic valve annulus and cusps can be approximated by modeling the aorta as a center cylinder, and the valve cusps circular portions as a hemisphere of the same radius, with the representative cusps intersecting at the center of the cylinder. Mathematically, the 3-dimensional geometry of the aorta is approximated by modeling the hemispheres (leaflets) with radius r and centered at (a,b,c) by the system of equations in spherical coordinates $(r,\theta,\phi)$:

$$x=a+r \sin \phi \cos \theta$$

$$y=b+r \sin \phi \sin \theta$$

$$z=c+r \cos \phi$$

$$r>0, 0\leq\theta<2\pi, 0\leq\phi\leq\pi$$

Furthermore, the cylinder (aorta) with radius r can also be modeled with a system of equations in cylindrical coordinates $(r,\vartheta,z)$:

$$x=r \cos \vartheta$$

$$y=r \sin \vartheta$$

$$z=z$$

$$r>0, 0\leq\vartheta<2\pi, -\infty<z<\infty$$

Intersection of two spheres of the same radius, r, centered at $(a_1,b_1,c_1)$ and $(a_2,b_2,c_2)$, is the solution of the system of equations:

$$a_1+r \sin \phi_1 \cos \theta_1=a_2+r \sin \phi_2 \cos \theta_2$$

$$b_1+r \sin \phi_1 \sin \theta_1=b_2+r \sin \phi_2 \sin \theta_2$$

$$c_1+r \cos \phi_1=c_2+r \cos \phi_2$$

The intersection of a sphere of radius, r, centered at (a,b,c), and a tube of the same radius is the solution of the system of equations:

$$a+r \sin \phi \cos \theta=r \sin \vartheta$$

$$b+r \sin \phi \sin \theta=r \cos \vartheta$$

$$c+r \cos \phi=z$$

With the model, the two above sets of equations can be solved to determine the points of intersection of the cusps with each other and with the aorta so as to produce a model having points of intersection as in FIG. 2a. Such model divides the aortic circumference into thirds, allows the cusps to meet centrally, and produces lateral overlap of the cusps in the same "coaptation crescent" as observed in the dissected specimens. Similarly, the results can be plotted to illustrate the intersection of a plane perpendicular to the axis of the aorta and the leaflets at multiple levels, and by stacking multiple 2-dimensional pictures, the 3-dimensional anatomy of the aortic valve leaflets can be viewed from above the valve as in FIG. 2b and from below the valve as illustrated in FIG. 2c. Furthermore, because the center of the base of the valve cusp hemispheres intersect the cylindrical aorta at the origin and the three valve cusp hemispheres each span approximately ⅓ of the circumference of the cylindrical aorta, a "shield shape" is produced for each cusp as illustrated in FIG. 3. Using this model, the 3-dimensional geometry of the normal aortic valve annulus can be determined using simple mathematics, by determining the intersections of the cusp hemispheres with the aortic cylinder.

Thus, the above relationships between the dimensions of the aortic valve and the cusps may be utilized in restoring valve competence. More specifically, the linear distance as measured on the dissected specimens is equal to about the modeled annular circumference, with the upper edge of an individual cusp equaling about ⅓ of the annular circumference. Furthermore, the cusp height was determined to be about equal to the annular radius of the hemispherical model.

By reducing annular geometry to this dimension, along with stenting the cusps to vertical and parallel, an aortic valve should be made competent, independent of existing root pathology. Thus, the inventive intra-annular hemispherical mounting frame may be utilized to restore the above discussed dimensional relationships of an incompetent valve to a competent aortic valve.

More particularly, the inventive intra-annular hemispherical mounting frame includes curvatures with curves in at least a first and a second plane to conform to the geometry of the cusps and also interconnecting points to conform to the normal commissural anatomy of the aortic valve. In one embodiment, three curvatures comprise the frame with each curvature adjoined to the other at a pointed peak conformed to the geometric characteristics of each commissure. In a preferred embodiment, a short post can extend up from each point to the commissure. These posts have a height that is equal to the equivalent radius of the aortic valve, and would suspend the commissure and each cusp in the proper three dimensional parallel relationships to allow complete coaptation.

The frame may be constructed of a variety of materials including metals, polymers, thermoplastics, plastics, and other materials which will allow for slight deformation but will not sheer under normal stresses. Conceivably, the frame could be a perforated strip of metal or plastic so as to allow the sutures better purchase upon mounting the frame.

Additionally, the frame may optionally be covered with a Dacron® cloth, thus utilizing the same materials as in current mitral valve annuloplasty ring designs, or alternatively, the frame may be covered with gluteraldehyde-fixed bovine pericardium or Gortex® material.

The intra-annular hemispherical mounting frames may embody a variety of sizes to match the intra-cusp volume and geometry of the aortic valve of different patients. In practical use, the intra-annular hemispherical mounting frame would range in sizes from about 16 millimeters to about 30 millimeters in most patients.

Generally, the intra-annular hemispherical mounting frame can be implanted into the aortic valve annulus in a variety of ways. A first method includes small fabric strips, pledgets, or pads with a combination of mattress sutures to firmly suture the intra-annular hemispherical mounting frame to the aortic valve annulus, while reducing tearing of the aortic tissue. Alternatively, complementary single cusp arcs with curvatures similar to the multiple shield curves may be employed above the cusps into which sutures may be inserted so that the patient's cusps would be "sandwiched" between the semi-rigid intra-annular hemispherical mounting frame and the supporting arcs above.

An object of the invention, therefore, is an intra-annular hemispherical mounting frame having characteristics which reconstruct the normal three-dimensional characteristics of the aortic valve.

Still another object of the invention is an intra-annular hemispherical mounting frame having curvatures with curves in at least a first and a second plane so that the frame is substantially conformed to the annular cusp geometry of the aortic valve.

Yet another object of the invention is an intra-annular hemispherical mounting frame having points interconnecting each curvature which conform to the geometry of the area around the commissures of the valve.

Another object of the invention is an intra-annular hemispherical mounting frame having posts corresponding to each interconnecting point which assists in suspending the commissures and cusps in a proper three-dimensional relationship.

Another object of the invention is a method of implanting the intra-annular hemispherical mounting frame to the aortic valve annulus with sutures extending from below the cusps to an area above the cusps.

Yet another object of the invention is a method of implanting the intra-annular hemispherical mounting frame which includes at least one support arc employed above the valve annulus similar in shape to the curvatures of the mounting frame.

Still another object of the invention is a method of modeling the intra-annular mounting frame by measuring at least one dimension of a patient's aortic valve.

Another object of the invention is a method of sizing the intra-annular mounting frame by an integration of modeling parameters into a diagnostic device.

These aspects and others that will become apparent to the artisan upon review of the following description can be accomplished through the use of an intra-annular hemispherical mounting frame designed with considerable consideration to the three-dimensional geometry of the aortic valve. The inventive intra-annular hemispherical mounting frame advantageously reconstructs proper cusp and commissure relations so that normal coaptation is achieved.

It is to be understood that both the forgoing general description and the following detailed description provide embodiments of the invention and are intended to provide an overview or framework of understanding the nature and character of the invention as is claimed.

DETAILED DESCRIPTION OF THE PREFERRED EMBODIMENTS

Although the products and methods according to the present invention are disclosed herein as being useful for and in the context of aortic valve repair, both the products and methodology may also be used in other fields including, but not limited to, surgical procedures for the repair of other valves within the human body.

Figure 4:
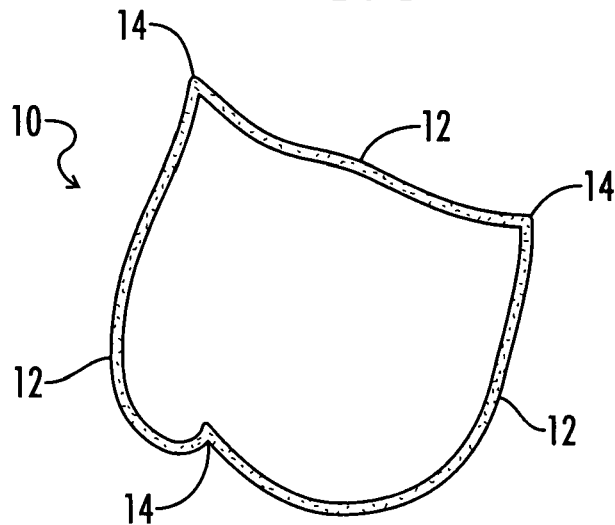
FIG. 4 is an illustration of one embodiment of the intra-annular hemispherical mounting frame.

Referring generally now to FIG. 4, an intra-annular hemispherical mounting frame useful for aortic valve repair is shown and generally designated as numeral 10. Intra-annular hemispherical mounting frame 10 is inserted into the aortic valve annulus and provides for the reconstruction of the native aortic valve.

Intra-annular hemispherical mounting frame 10 includes a plurality of curvatures 12 and also interconnecting points 14. Generally, curvature 12 conforms to the annular cusp geometry with interconnecting points 14 conforming to the geometry of the commissures. Curvatures 12 curve in about a first plane and a second plane of hemispherical mounting frame 10 to correspond to the three-dimensional geometry of the cusps of an aortic valve. For reference, the latitudinal plane is defined as the horizontal plane on which intra-annular hemispherical mounting frame 10 would rest with each curvature 12 contacting the latitudinal plane similarly. The longitudinal plane is defined as the plane which intersects the latitudinal plane at a perpendicular angle and runs vertically through intra-annular hemispherical mounting frame 10. Curvatures 12 may curve in both the latitudinal and longitudinal planes and in optional embodiments the curvatures may curve in multiple other planes. Preferably, curvature 12 curves in at least two planes to correspond to the three-dimensional geometry of the aortic valve with curvature 12 in contact with the wall while providing support and alignment to the aortic valve cusps. Furthermore, interconnecting points 14 serve the dual function of interconnecting curvatures 12 while also providing support to the commissures of the aortic valve. Specifically, interconnecting points 14 are designed to closely fit the three-dimensional geometry between adjacent cusps and locate near the commissures thus providing support and assistance in the restoration of the proper coaptation of the cusps. Each point of interconnecting points 14 continuously narrows into a tip so that each point fits within the narrowing space between adjacent cusps which culminates in a commissure. As such, interconnecting points 14 provide support within this inter-cusp space to immediately below the commissures.

Figure 5:
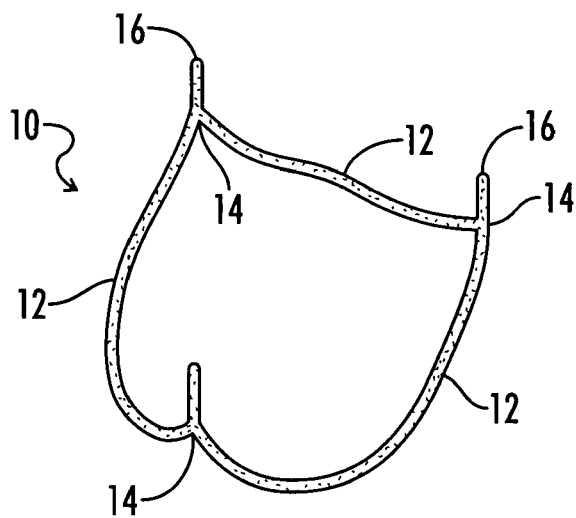
FIG. 5 is an illustration of a preferred embodiment of the intra-annular hemispherical mounting frame.

FIG. 5 illustrates a preferred embodiment of intra-annular hemispherical mounting frame 10 with posts 16 extending up from interconnecting points 14. Posts 16 function as to suspend the commissures of the aortic valve as well as the cusps in proper three-dimensional parallel relationships to allow complete coaptation when implanted in an aortic valve. Different from the embodiment in FIG. 4, interconnecting points 14 of the embodiment displayed in FIG. 5. do not extend significantly into the narrowing space between adjacent cusps, but rather posts 16 extend as such. Otherwise stated, the tip of interconnection points 14 of FIG. 4 is at about the same height as the tip of post 16 of the embodiment in FIG. 5. In order to fully understand the design characteristics of the multiple embodiments of intra-annular hemispherical mounting frame 10, it is necessary to understand and consider the three-dimensional relationships within the anatomy of the aortic valve.

Figure 6:
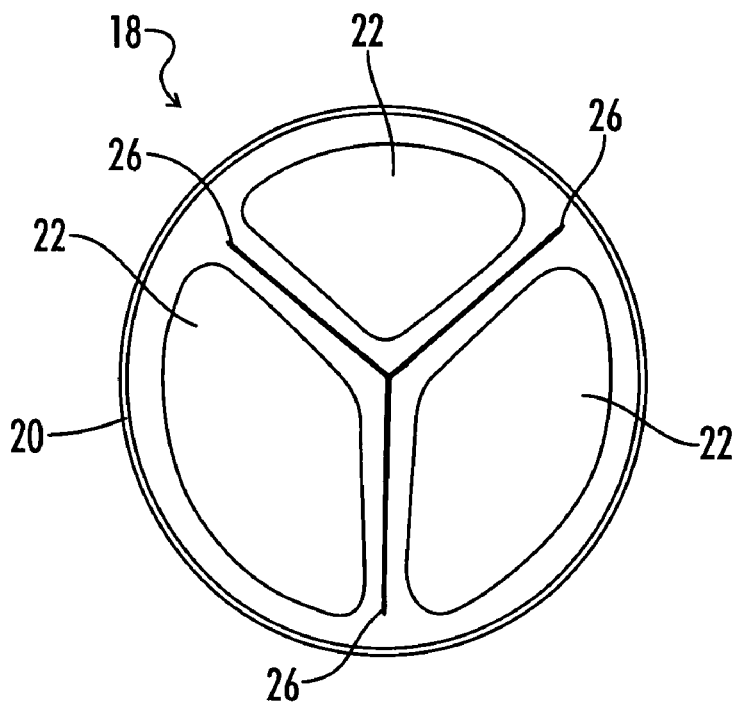
FIG. 6 is an illustration of a supra-valvular view of normal aortic valve.

FIG. 6 illustrates a cross-sectional view of normal aortic valve 18 with aortic wall 20, cusps 22 and commissures 26. Aortic valve 18, while not perfectly circular in actuality, is most often within the art, prescribed measurements typically attributable to a cylindrical object in order to provide ease in the measurements and calculations associated with aortic valve 18. As such, each of cusps 22 attach to about one-third of the circumference of aortic wall 20 while meeting in coaptation in the center of aortic valve 18. Commissures 26 are defined as the juncture points where adjacent cusps 22 attach to aortic wall 20. While FIG. 6 only illustrates the two-dimensional aspects of normal aortic valve 18, a complex three-dimensional orientation is necessary for both cusps 22 and commissures 26 to align in the proper coaptation as is illustrated.

Figure 7:
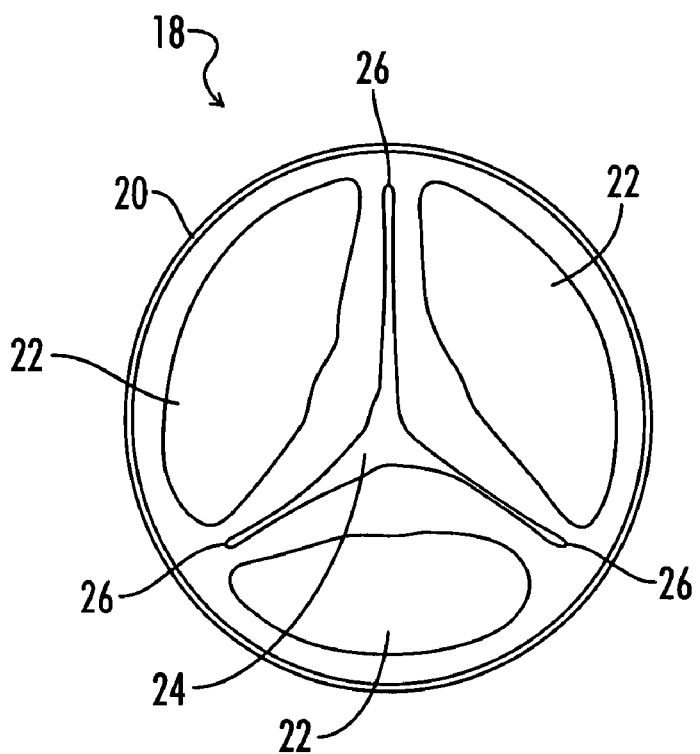
FIG. 7 is an illustration of a supra-valvular view of a diseased aortic valve.

FIG. 7 illustrates a cross-sectional view of a diseased aortic valve with aortic wall 20, cusps 22, and also aortic valve leak 24. Leak 24, as illustrated in FIG. 7, may be a result of dilation of aortic annulus 18, and as a result, cusps 22 do not meet in the proper coaptation. Essentially, leak 24 is a central gap of coaptation, resulting in aortic insufficiency which in turn increases the annular dilation of aortic valve 18 thus progressively increasing leak 24.

Figure 8:
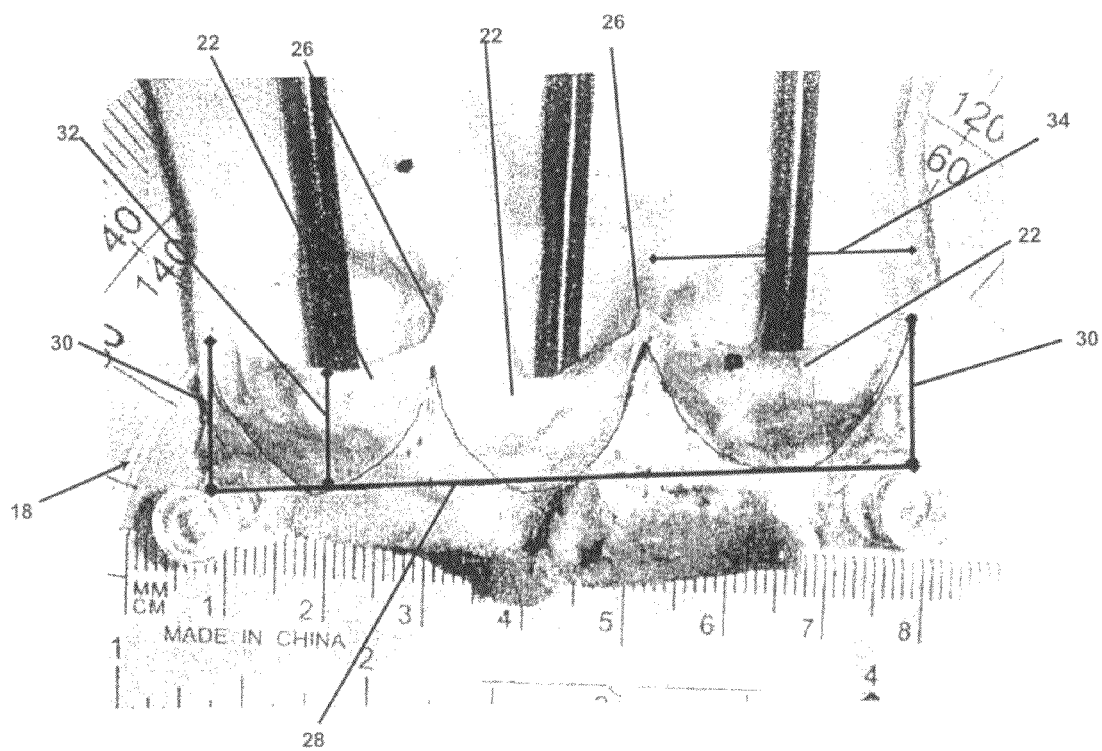
FIG. 8 is an illustration of a dissected aortic valve opened longitudinally through a commissure.

Turning now to FIG. 8, FIG. 8 is an illustration of a dissected aortic valve 18, opened longitudinally through commissure 26 between two cusps 22 and laid flat. Each of the three cusps 22 is illustrated as a "shield-shaped flap" with the two intact commissures 26 visible where the adjacent cusps 22 contact to form a point and attach to the aortic wall. Aortic valve 18 is physically characterized by annular circumference 28 which is the measurement of the linear distance from one aortic margin 30 to the other aortic margin 30 at the approximate base of cusps 22. From the annular circumference, the annular diameter and annular radius can be calculated to further define the physical geometry of the aortic valve. Furthermore measurements include cusp height 32 which is defined as the distance from the approximate base of cusp 22 to upper midpoint of cusp 22 which is generally found to be within 1 millimeter of the annular radius in a normal functioning aortic valve. Cusp length 34 is approximately the measurement of cusp 22 free edge from one commissure 26 to the next and is also about equal to annular circumference 28 divided by 3 as three cusps 22 comprise the length of annular circumference 28.

Figure 1:
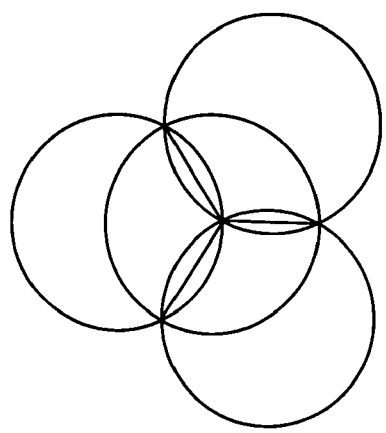
FIG. 1 is a 2-dimensional illustration of the top view of the hemispherical model of the aortic valve.
Figure 2A:
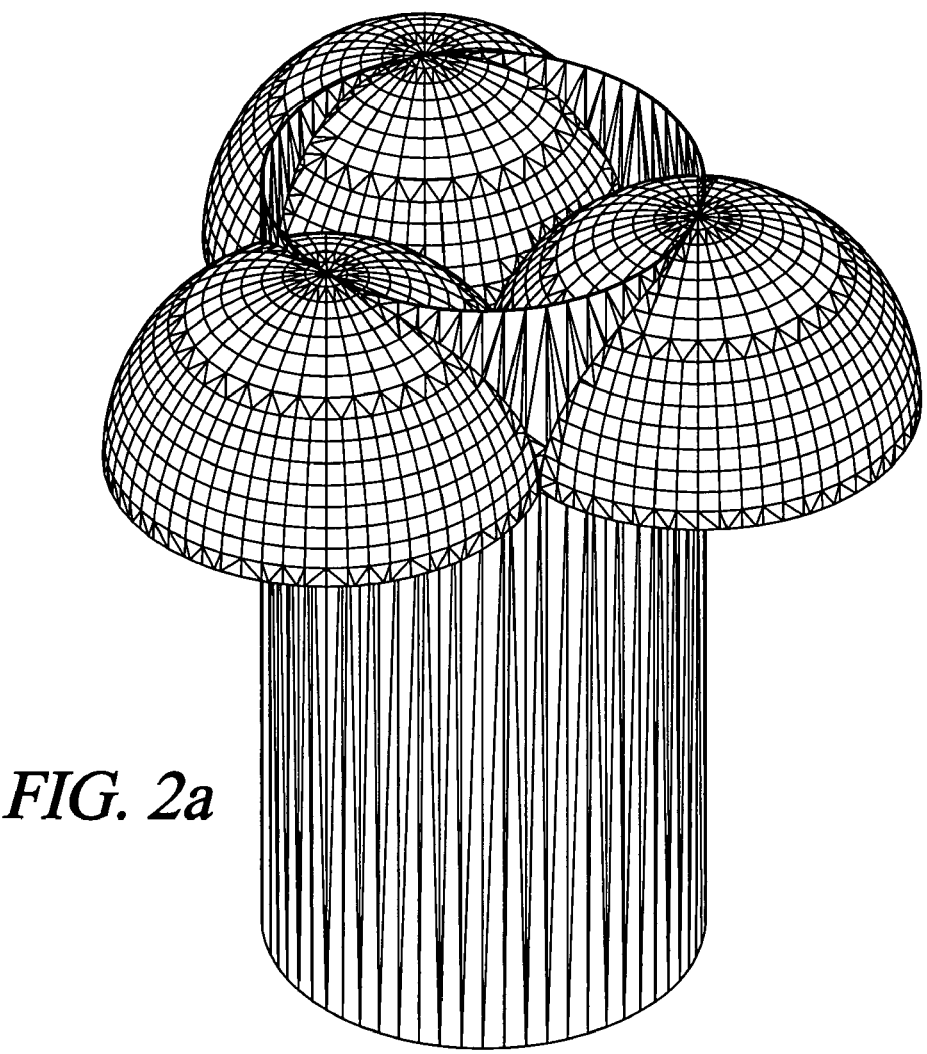
FIG. 2a is an illustration of a side-top view of a cylindrical aortic model.
Figure 2B:
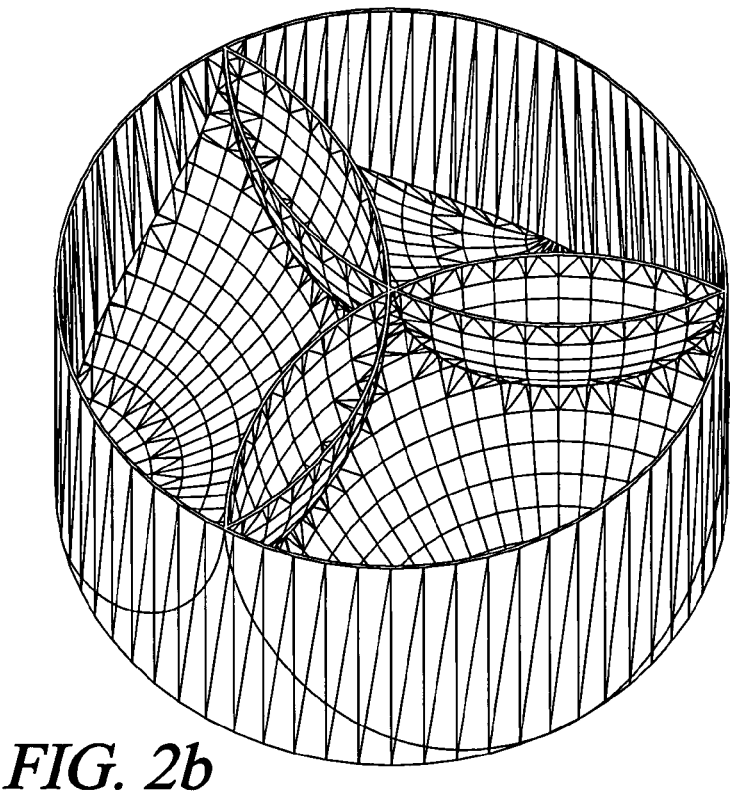
FIG. 2b is an illustration of 3-dimensional anatomy of the aortic valve viewed from above the valve.
Figure 2C:
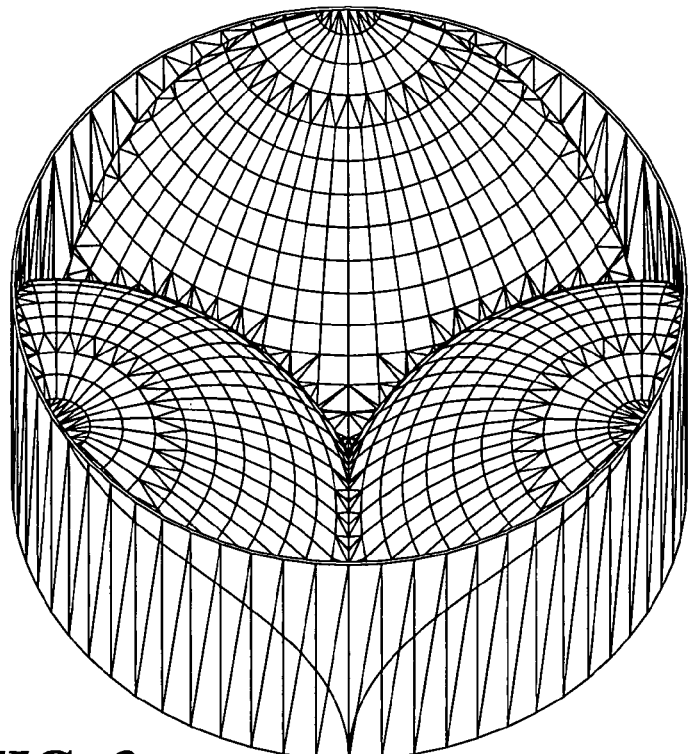
FIG. 2c is an illustration of 3-dimensional anatomy of the aortic valve viewed from below the valve.
Figure 3:
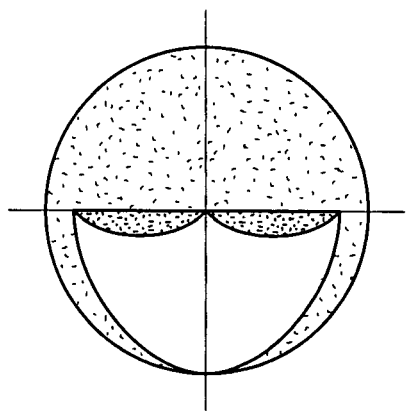
FIG. 3 is an illustration of a model of a cusp.
Figure 9:
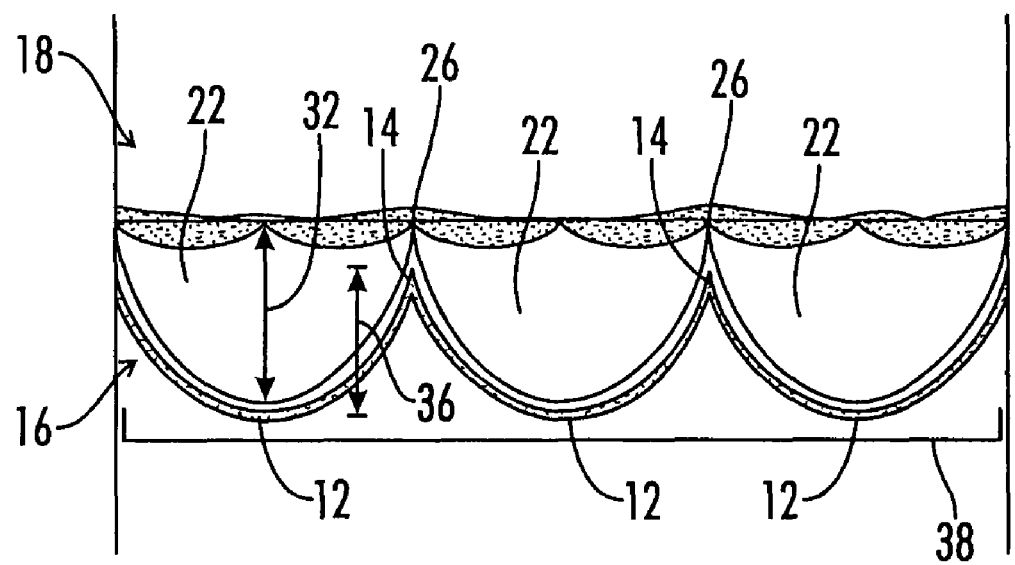
FIG. 9 illustrates a first embodiment of the intra-annular hemispherical mounting frame in a longitudinally opened position, overlaid on a longitudinally opened normal aortic valve and laid flat.

These measurements and calculations were utilized to form intra-annular hemispherical mounting frame 10 as illustrated in FIG. 3, which is further illustrated two-dimensionally in FIG. 9 in a longitudinally opened position, overlaid on a longitudinally opened normal aortic valve and laid flat. While intra-annular hemispherical mounting frame 10 of the present invention does not open or break in practice, the two dimensional, longitudinally open view of FIG. 9 provides for greater ease in illustrating the dimensional aspects of intra-annular hemispherical mounting frame 10 in relation to aortic valve 18. Each of three curvatures 12 are positioned approximately adjacent to the three bases of cusps 22 of aortic valve 18. The base cusps curvatures 12 have an incident of curvature approximately similar to the curve at which cusps 22 attach to the aortic wall. While not illustrated, in an intact aortic valve, curvatures 12 would also curve in at least one additional plane thus corresponding to the three dimensions of an intact aortic valve. Additionally, the two intact commissure points 14, as well as the additional commissure point 14 not shown, fit substantially up to each respective commissure 26 of aortic valve 18. Intra-annular hemispherical mounting frame 10 height 36 is the approximate distance from the base of each curvature 12 to each interconnecting point 14 which is similar to cusp height 32 of the aortic valve 18. Furthermore, intra-annular hemispherical mounting frame 10 length 38 is similar in geometry and dimensions to the annular circumference 28 of aortic valve 18.

Figure 10:
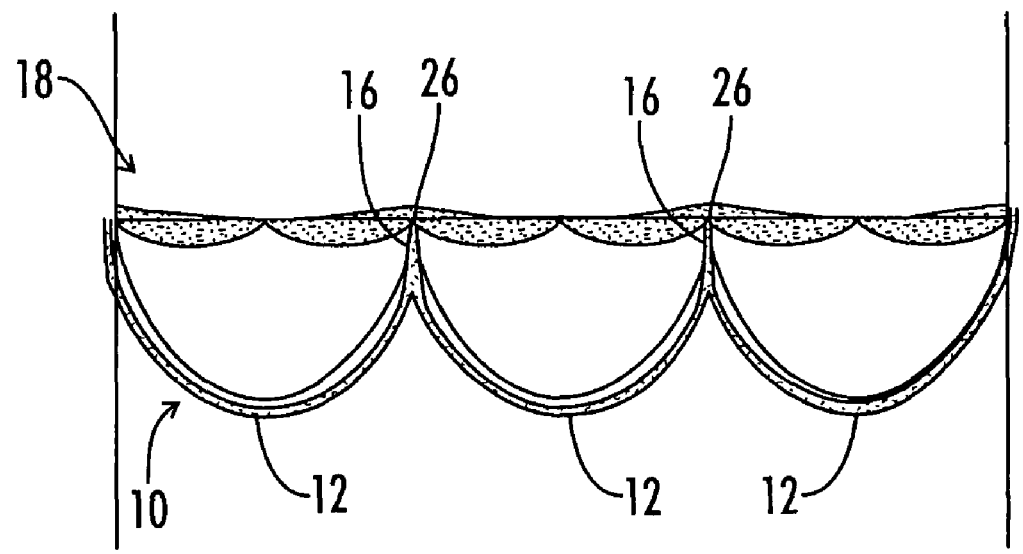
FIG. 10 illustrates a second embodiment of the intra-annular hemispherical mounting frame in a longitudinally opened position, overlaid on a longitudinally opened normal aortic valve and laid flat.

In another aspect of the invention, FIG. 10 represents the embodiment illustrated in FIG. 5 in a two-dimensional longitudinally open view similar to the embodiment of FIG. 4 illustrated in FIG. 9. With this embodiment, posts 16 may extend up to the commissures 26 or slightly past. Most preferably, posts 16 may be of a height equal to the radius of the aortic valve 18 and may suspend the cusps in proper three dimensional parallel relationships to allow for complete coaptation of the aortic valve.

Figure 13:
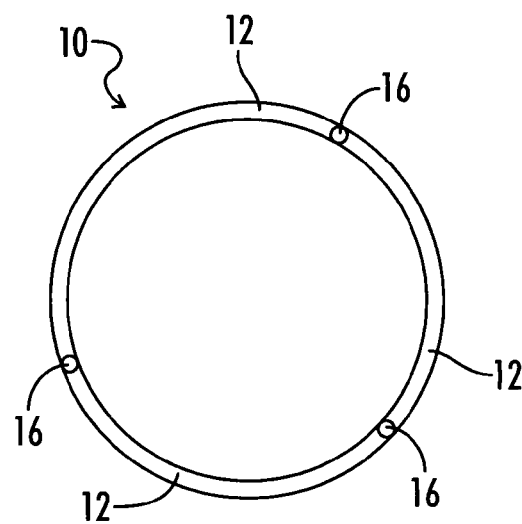
FIG. 13 illustrates a top view of the second embodiment of the intra-annular hemispherical mounting frame.

Generally, intra-annular hemispherical mounting frame 10 as embodied in FIG. 4 and FIG. 5 as well as in additional embodiments is substantially similar in geometry and dimensions to a normal aortic valve. Most often the intra-annular hemispherical mounting frame will be sized about 2 millimeters less in diameter than the calculated diameter of the aortic valve (based on the leaflet free edge length) into which the intra-annular hemispherical mounting frame will be implanted, while the incident of curvature of each of the three curvatures will be similar to the base of the cusps or can be slightly greater or lesser, partially depending on whether the intra-annular hemispherical mounting frame includes posts or not on the commissure points and also partially depending on the degree of abnormality of the aortic valve. The intra-annular hemispherical mounting frame can be produced in a variety of sizes and embodiments for providing the correct coaptation of the cusps of the aortic valve. The intra-annular hemispherical mounting frame circumferential length may be of a variety of sizes depending of the necessary alteration of the geometry of the diseased aortic valve. While the intra-annular hemispherical mounting frame may be considered generally circular when viewed from above as illustrated in FIG. 13, which is a top view of the embodiment of the intra-annular hemispherical mounting frame displayed in FIG. 5, the frame may include minor deviations from a circular arrangement, including deviations such as structural flaring. Despite these deviations, the measurement types prescribed to a cylinder will be utilized with regard to the intra-annular hemispherical mounting frame.

Most generally, the diameter of the intra-annular hemispherical mounting frame is from about 16 millimeters to about 30 millimeters with a variety of different sized frames there between, forming a gradient of possible choices to closely approximate the needs of the patient. Large sizes of the intra-annular hemispherical mounting frame would be produced so that the invention could be utilized with aortic root aneurysms or patients with Marfan syndrome. Furthermore, the intra-annular hemispherical mounting frame height as measured from the base of a curvature to the commissure point may vary, most often being equivalent to the calculated radius of the repaired valve. Thus, the embodiment as illustrated in FIG. 4, with the intra-annular hemispherical mounting frame of FIG. 5. would have a measurement from the base of the curvature to the top of a post from about (but not exclusively) 8 millimeters to about 15 millimeters. The posts on the commissure points may be perpendicular to the longitudinal plane of the intra-annular hemispherical mounting frame and in additional embodiments may angle toward the interior area of the intra-annular hemispherical mounting frame or outward away from the interior area of the intra-annular hemispherical mounting frame. The posts may extend away from the interior area of the frame at an angle of from about 90 degrees to about 120 degrees when measured from the internal area of a latitudinal plane of the frame. Different orientations and shapes of both the posts as well as the shapes of the curvatures may be utilized to account for the different anatomic variations. In most embodiments, the curvatures would be fairly symmetrical to one another as most valves have 3 cusps of equal sizes, though in additional embodiments the intra-annular hemispherical mounting frame can be produced in an asymmetrical design as some patients have asymmetrical sinuses. Variations could include an intra-annular hemispherical mounting frame with one curvature about 20% larger than the other two curvatures, and also a variation with a single curvature sized 20% smaller than the other curvatures. Additionally, the intra-annular hemispherical mounting frame may be produced with two curvatures and two interconnecting points for valves where only two cusps are present. Furthermore, additional embodiments can include a Gore-Tex® coating of the frame as well as include the use of a variety of different polymers to coat the frame's surface.

Generally, the intra-annular hemispherical mounting frame's curvatures may curve in at least two planes as the location of the intra-annular hemispherical mounting frame within the aortic valve necessitates correspondence to both the curves of the aortic wall and cusps of the aortic valve, for proper coaptation.

The intra-annular hemispherical mounting frame is comprised of metal, plastics, thermoplastics, polymers, resins or other materials which will remain intact in spite of potentially high tension caused from a highly dilated aortic roots. Preferably the intra-annular hemispherical mounting frame may be constructed of a solid metal wire, solid plastic, and most preferably a perforated strip of metal or plastic so as to provide the sutures better purchase once implanted into the aortic valve. The perforations may vary depending on the installation method, though preferably with the fairly uniform geometry of the annular region, a set number and position of perforations for sutures may be created and marked onto the intra-annular hemispherical mounting frame.

In further embodiments, the intra-annular hemispherical mounting frame may be covered with a variety of polymers or polymer resins, including but not limited to polyethylene terephthalate, sold under the name Dacron® cloth. Dacron® cloth is generally employed with mitral rings used in mitral valve repair. Alternatively, the intra-annular hemispherical mounting frame may be covered with gluteraldehyde-fixed bovine pericardium which is useful as high blood velocities in the outflow tract of the left ventricle could possibly predispose the patient to hemolysis with a cloth covering.

Generally, the novel intra-annular hemispherical mounting frame allows repair in even the most dilated aortic roots, and can permanently stent and support the three dimensional geometry of the aortic root so that further dilatation and late failure would not occur. Regarding the embodiment of the intra-annular hemispherical mounting frame having posts extending from the interconnecting points, the posts generally have a length of from about 70% to about 130% of the radius of the aortic valve, and are usually of about a length equal to the radius of the valve. More specifically, the intra-annular hemispherical mounting frame can approximate the radius of a competent aortic valve and thus increase or decrease the valve size of the diseased aortic valve to restore valve competency. In sizing the intra-annular hemispherical mounting frame, the top circumference of a cusp may be measured and then tripled to obtain a general circumference of the aortic valve. Most preferably, 2 millimeters to about 8 millimeters will be subtracted from this general circumference of the aortic valve to determine the frame circumference of the intra-annular hemispherical mounting frame. The subtraction of from about 2 to about 8 millimeters is preferable as this undersizes the frame from about 0.67 millimeters to about 2.33 millimeters per cusp and approximately from about 0.67 millimeters to about 2.33 millimeters in diameter of the valve, thus allowing for the reorientation of the valve to provide greater cusp area of coaptation and valve competency. In this situation, suturing the commissural aspects of the cusps to the embodiment of the intra-annular hemispherical mounting frame with posts can eliminate much of the intercommissural dimension. Generally, the intra-annular hemispherical mounting frame will reorient the native annulus to about a diameter of from about 16 millimeters to about 27 millimeters, and preferably of from about 18 millimeters to about 25 millimeters in most patients, though reorienting the aortic valve to a diameter of less than about 18 millimeters and lower generally will be avoided in order to prevent systolic gradients. Furthermore, the intra-annular hemispherical mounting frame may be utilized to restore competency to prolapsed valves, wherein the diseased valve cusp is raised up and restored to a proper orientation within the aortic wall by adjusting the spacing of the annular sutures in the frame.

One of the many advantages of the intra-annular hemispherical mounting frame, is the ease in which the required frame size can be determined preoperatively. Imaging techniques such as Magnetic Resonance Imaging (MRI) can be used, non-invasively, to determine the measurements of the patient's aortic valve cusp free edge. More specifically, the measurement of an aortic valve cusp, from one annular commissure to the other, should be equal to the one-third of the desired valve circumference and also approximately equal to the annular diameter of the valve, with the height of each commissure roughly equivalent to the annular radius. As such, the size of the intra-annular hemispherical mounting frame may be determined by measuring the top circumference of a cusp of the aortic valve of a patient through MRI, echocardiography, or other techniques, tripling the measured top circumference of a cusp to obtain a desired annular circumference of the diseased aortic valve, and then reducing the overall circumference with the frame to provide competency. Typically, a frame would be selecting with a circumference from about 2 mm to about 8 mm less than that calculated from the cusp length. This would provide a circumference which could be converted to diameter by which a variety of different sized intra-annular hemispherical mounting frame may be organized.

In further embodiments the imaging device, including an MRI machine and related controls, could include system parameters and mathematical descriptions of the hemispherical model which automatically take the measurements of the patient's aortic valve and output the appropriately sized intra-annular hemispherical mounting frame required to restore competency of the patient's aortic valve. Additional data output could include the display of varying sized intra-annular hemispherical mounting frames for restoring competency and the reduction in annular diameter each different frame would create upon implantation.

Figure 11:
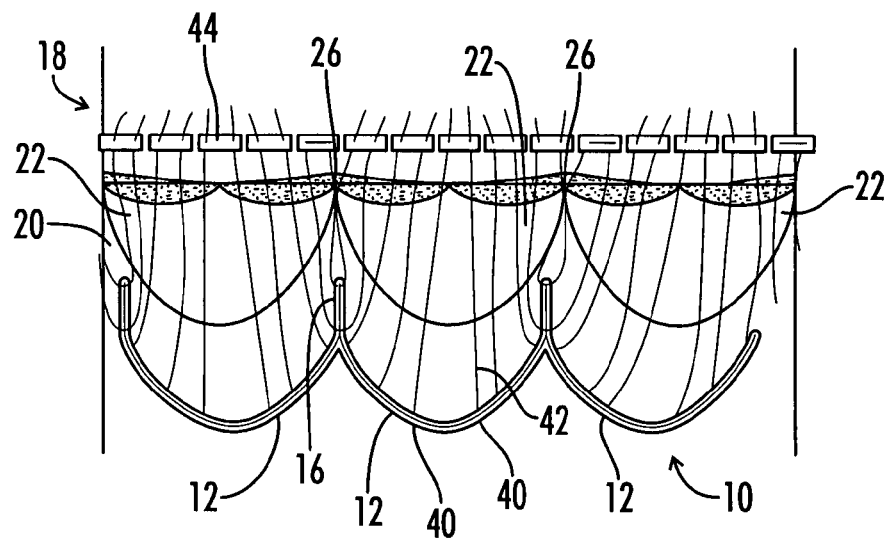
FIG. 11 illustrates a first embodiment of mounting the intra-annular hemispherical mounting frame opened to display a suture configuration with an aortic valve.

Referring now to FIG. 11, there is shown intra-annular hemispherical mounting frame 10 opened to display a suture configuration in two dimensions with aortic valve 18. Intra-annular hemispherical mounting frame 10 may have perforations 40 on curvatures 12 and posts 16 for the passage of sutures 42 therethrough. Sutures 42 may be horizontal mattress sutures which may then pass into the aortic wall beneath the aortic valve annulus 20. In a preferable arrangement, sutures 42 would pass deep into the aortic wall, under cusps 22, allowing for the insertion of intra-annular hemispherical mounting frame 10 directly into aortic valve annulus 18 which would closely correspond to the cusps 22 and commissures 26. Optionally, 3 horizontal mattress sutures may be utilized per cusp 22 and one per commissure 26 with a total of 12 sutures used to implant intra-annular hemispherical mounting frame 10. Obviously, lesser or more sutures as well as other attachment techniques known in the art may be utilized to position and attach intra-annular hemispherical mounting frame 10 into aortic valve annulus 18. Above valve 18, pledgets 44 may be placed onto the mattress sutures to preclude the possible tearing of aortic tissue. Pledgets 44 may be Teflon® felt pledgets or in other embodiments not illustrated; pieces or strips of fabric may be utilized with the mattress sutures rather than pledgets. Preferably, pledgets 44 may be small so they would not interfere with the mobility of the aortic valve leaflets.

Figure 12:
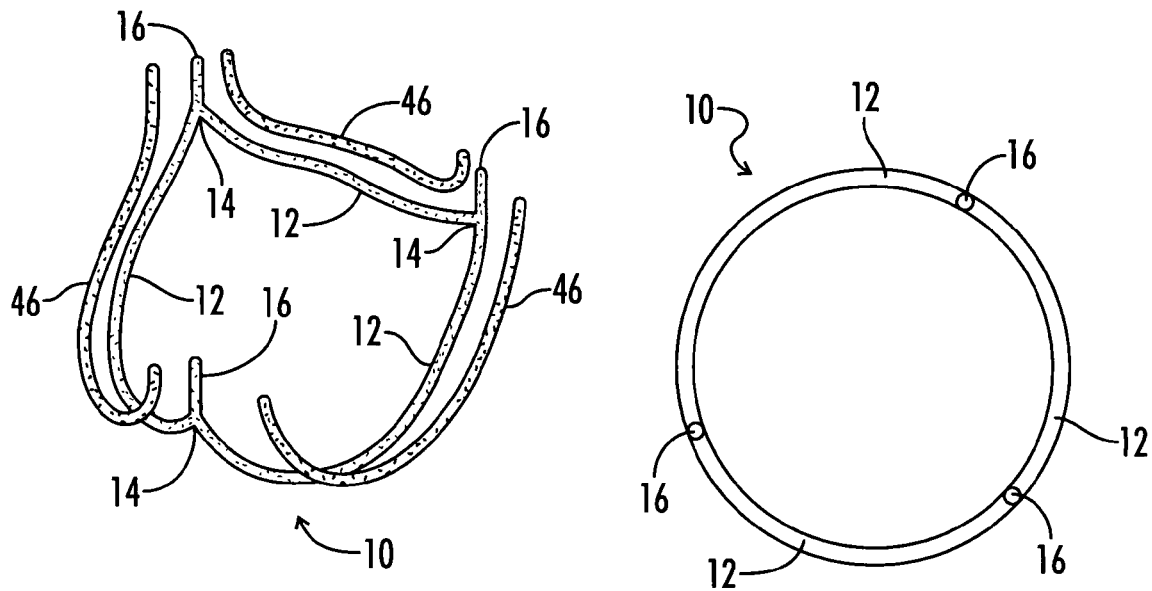
FIG. 12 illustrates a second embodiment of mounting the intra-annular hemispherical mounting frame.

Referring now to FIG. 12, there is shown an alternative embodiment for installing intra-annular hemispherical mounting frame 10. Support arcs 46 may be employed above the valve annulus, into which sutures could be inserted. Support arcs 46 may comprise three curvatures with a shape that is substantially similar to intra-annular hemispherical mounting frame which corresponds to the curvature and geometry of the attachment of the cusps to the aortic wall as well as the commissures, resulting in the annulus of the aortic valve being "sandwiched" between intra-annular hemispherical mounting frame 10 and support arcs 46. Sutures may extend through perforations in the intra-annular hemispherical mounting frame through the aortic wall to the support arcs above the cusps, attaching also through perforations in the support arcs. In additional embodiments, the sutures may extend around the support arcs or attach in other methods known in the art.

While the novel intra-annular hemispherical mounting frame and related methods of sizing and implanting the intra-annular hemispherical mounting frame have been discussed, the invention could also be applied to other pathologies. With aortic root aneurysms, the annuloplasty frame could allow leaflet-sparing root replacement to be performed totally from inside the aorta, without the need for extensive external dissection, as with current procedures. A non-porous Dacron® graft may be utilized with the intra-annular hemispherical mounting frame after being scalloped and flared in the graft's proximal aspect, to conform to the sinuses of Valsalva. The size of the graft may be selected to match the size of the intra-annular hemispherical mounting frame, with consideration also being given for the diameter of the distal aorta.

The coronary arteries could then would be anastomosed to the side of the graft, either as buttons or with the inclusion technique. Using this simple method, the aortic valve annulus would be fixed in size and geometry, the native aortic valve would be repaired and preserved, and the entire root and ascending aorta could be replaced for root aneurismal disease, with much less dissection and difficulty than with current techniques.

Other pathologies also could be approached. Ultrasonic debridement could be used adjunctively to remove spicules of calcium, and portions of leaflets could be resected and replaced with gluteraldehyde-fixed autologous pericardium. This concept also raises the issue of aortic valve single cusp replacement. With a method of fixing root geometry through reorientation, and potentially undersizing it slightly, more complex repairs could be undertaken, with the frame annuloplasty compensating for slight imperfections. If one cusp were severely diseased or prolapsing, for example, the cusp could be replaced with a gluteraldehyde-fixed bovine pericardial cusp (of the appropriate size and geometry to match the size of the frame and native cusps). The artificial cusp could be attached to the arc above the annuloplasty frame, with the frame acting as an attachment for the arc and artificial leaflet. Alternatively, frames could be manufactured with one bovine pericardial cusp attached to one sinus. The patient's other valve tissue could be spared, and an entirely competent valve achieved, which then would be two-thirds native tissue. The pericardial leaflet tissue could be treated with contemporary techniques for preventing calcification, but if the artificial leaflet became immobile late postoperatively, it still could act as a coaptation baffle for the other leaflets, and possibly not require additional operations, as can occur with total heterograft replacement.

The intra-annular hemispherical mounting frame is unique as compared to other apparatuses used in aortic valve repair, as the intra-annular hemispherical mounting frame is designed with regard to the three-dimensional nature of the aortic valve, providing the proper anatomic geometry to the cusps and commissures to create the necessary orientation to provide valve competence. The intra-annular hemispherical mounting frame mounts directly to the annulus within the patient's own valve and returns the geometry of the cusps to a normal condition. Through the use of the intra-annular hemispherical mounting frame's interconnecting points and preferably, the inclusion of narrow posts (the interconnecting points), the commissural aspect of the annulus may be raised to a proper height and orientation to produce normal cusp geometry and coaptation.

Accordingly, by the practice of the present invention, an apparatus for restoring normal valve geometry having heretofore unrecognized characteristics is disclosed. Furthermore, the invention includes the proper sizing and multiple implantation methods of the intra-annular hemispherical mounting frame for the restoration of normal valve geometry.

The disclosures of all cited patents and publications referred to in this application are incorporated herein by reference.

The above description is intended to enable the person skilled in the art to practice the invention. It is not intended to detail all of the possible variations and modifications that will become apparent to the skilled worker upon reading the description. It is intended, however, that all such modifications and variations be included within the scope of the invention that is defined by the following claims. The claims are intended to cover the indicated elements and steps in any arrangement or sequence that is effective to meet the objectives intended for the invention, unless the context specifically indicates the contrary.

What is claimed is:

1. An intra-annular mounting frame for an aortic valve having native aortic cusps, comprising:
   a frame body including native leaflet reorienting curvatures and interconnecting points and posts;
   the curvatures shaped to be received inside the valve below the native aortic cusps and to reorient the native aortic cusps within the aortic valve;
   each of the curvatures extending only concavely upward from a reference latitudinal plane tangential to each curvature's base;
   the interconnecting points connecting the curvatures to form the mounting frame; and
   the posts extending radially outward from a central longitudinal axis of the frame.

2. The mounting frame of claim 1 wherein the frame comprises three curvatures and three points.

3. The mounting frame of claim 1 wherein the frame comprises two curvatures and two points.

4. The mounting frame of claim 1 wherein one of the posts extends from each of the points.

5. The mounting frame of claim 4 wherein the posts extend away from the interior area of the frame at an angle of from about 90 degrees to about 120 degrees measured from the internal area of a latitudinal plane of the frame.

6. The mounting frame of claim 1 wherein each post comprises a length equal to about the radius of the valve.

7. The mounting frame of claim 1 wherein each post comprises a length of about 70% to about 130% of the radius of the valve.

8. The mounting frame of claim 1 wherein the length of the post is of from about 8 millimeters to about 16 millimeters.

9. The mounting frame of claim 1 wherein the frame has a circumference of about the circumference of the valve.

10. The mounting frame of claim 1 wherein the frame has a diameter of about 16 millimeters to about 30 millimeters.

11. The mounting frame of claim 1 wherein the frame has a diameter less than the diameter of the valve.

12. The mounting frame of claim 9 wherein the frame has a diameter of about 2 millimeters to about 8 millimeters less than the diameter of the valve.

13. The mounting frame of claim 1 wherein the frame is comprised of metal.

14. The mounting frame of claim 11 wherein the frame comprises metal wire.

15. The mounting frame of claim 1 wherein the frame is comprised of a material selected from the group consisting of plastics, polymers, metal, thermoplastics, resins, and combinations thereof.

16. The mounting frame of claim 1 wherein the frame further comprises perforations through the frame.

17. The mounting frame of claim 1 further comprising a surface covering of polymer-type fiber cloth.

18. The mounting frame of claim 1 further comprising a surface covering of gluteraldehyde-fixed bovine pericardium.

19. The mounting frame of claim 1 wherein each post extends toward a commissure of the aortic valve.

20. The mounting frame of claim 1 wherein each interconnecting point comprises a continuously narrowing tip which connects adjacent curvatures to form the mounting frame.

21. An intra-annular mounting frame for an aortic valve having native aortic cusps, comprising:
    a frame body including native leaflet reorienting curvatures and interconnecting points and posts;
    the curvatures shaped to be received inside the valve below the native aortic cusps and to reorient the native aortic cusps within the aortic valve;
    each of the curvatures extending only concavely upward from a reference latitudinal plane tangential to each curvature's base;
    the interconnecting points connecting the curvatures to form the mounting frame; and
    the posts extending radially outward at about greater than 90 degrees to about 120 degrees from the reference latitudinal plane.

22. The intra-annular mounting frame of claim 18 wherein each post comprises a length equal to about the radius of the valve.

23. An intra-annular mounting frame for an aortic valve having native aortic cusps, comprising:
    a frame body including native leaflet reorienting curvatures and interconnecting points with each interconnecting point extending into a continually narrowing tip;
    the curvatures shaped to be received inside the valve below the native aortic cusps and to reorient the native aortic cusps within the aortic valve;

each of the curvatures extending only concavely upward from a reference latitudinal plane tangential to each curvature's base;

the interconnecting points connecting the curvatures to form the mounting frame; and the continually narrowing tips extending radially outward from a central longitudinal axis of the frame.

24. An intra-annular mounting frame for an aortic valve having native aortic cusps, comprising:

a frame body including native leaflet reorienting curvatures and interconnecting points each extending into a continually narrowing tip;

the curvatures shaped to be received inside the valve below the native aortic cusps and to reorient the native aortic cusps within the aortic valve;

each of the curvatures extending only concavely upward from a reference latitudinal plane tangential to each curvature's base;

the interconnecting points connecting the curvatures to form the mounting frame; and the continually narrowing tips extending radially outward at about greater than 90 degrees to about 120 degrees from the reference latitudinal plane.

* * * * *